United States Patent [19]

Hunt

[11] Patent Number: 4,519,249
[45] Date of Patent: May 28, 1985

[54] APPARATUS FOR DETECTING THE CONDITION OF A SHEET OR WEB

[75] Inventor: Steven A. Hunt, Petersfield, England

[73] Assignee: De la Rue Systems Limited, London, England

[21] Appl. No.: 508,188

[22] Filed: Jun. 27, 1983

[30] Foreign Application Priority Data

Jun. 28, 1982 [GB] United Kingdom ............... 8218618

[51] Int. Cl.³ ............................................. G01N 29/04
[52] U.S. Cl. ....................................... 73/596; 73/627; 73/159
[58] Field of Search .............. 73/104, 105, 159, 627, 73/628, 629, 596

[56] References Cited

U.S. PATENT DOCUMENTS

| | | | |
|---|---|---|---|
| 2,769,158 | 10/1956 | Schultz | 73/627 |
| 3,477,288 | 11/1969 | Krcal et al. | 73/159 |
| 4,080,839 | 3/1978 | Schaiber et al. | 73/627 |
| 4,111,053 | 9/1978 | Geithman et al. | 73/588 |
| 4,446,735 | 5/1984 | Weilacher | 73/159 |

FOREIGN PATENT DOCUMENTS

| | | |
|---|---|---|
| 0073133 | 3/1983 | European Pat. Off. |
| 2156077 | 12/1976 | Fed. Rep. of Germany |
| 828840 | 2/1960 | United Kingdom |

OTHER PUBLICATIONS

"Soviet Inventions Illustrated", Article A3846C/02, Week C 02, 20 Feb. 1980, Section R16 & SU-A-658466.

Primary Examiner—Anthony V. Ciarlante
Attorney, Agent, or Firm—Cushman, Darby & Cushman

[57] ABSTRACT

For the detection of defects such as tears or fold lines in banknotes, for example, continuous wave ultrasonic energy is directed by a transmitter to a flow path for the notes and ultrasonic energy reflected from the notes or transmitted through tears or holes in the notes is converted by a receiver into an electric signal. A signal analyzing circuit is responsive to changes in the output of the receiver during the passage of the banknote. In the ultrasonic inspection area, the note may be passed over rollers with flared ends to cause a tear to open and allow the passage of ultrasonic energy. In a reflective system the note may be passed over a roller to cause one or both of the adjacent edges of a tear to leave the roller surface. The electric signal is analyzed for components indicative of a defect; for tear detection, a spike filter and a circuit for distinguishing tear signals from end-of-note signals may be used. For crinkle detection, the received signal may pass through a differentiator, an integrator and a threshold comparator.

10 Claims, 10 Drawing Figures

APPARATUS FOR DETECTING THE CONDITION OF A SHEET OR WEB

This invention relates to the detection of defects in sheets or in a web and has a particularly important application in the detection of defects in banknotes.

It has previously been proposed in British patent specification No. 1181047 to detect increased thickness in a web, running between guides, by comparing the variable path length from an ultrasonic transmitter transmitting ultrasonic energy through an aperture in an upper guide to a receiver for receiving ultrasonic energy reflected back from the web through the aperture, with a fixed path length defined by a similar reference ultrasonic transmitter/receiver system. The changes in the thickness of the web are detected by comparing the phase of the ultrasonic signals which have travelled the path length to the web and back with the phase of the ultrasonic signals of the reference system which have travelled the fixed path length. Such a detector requires a precision which would be difficult to achieve with individual sheets and in particular with used banknotes; in this prior specification it is proposed to use, in addition to the second transmitter/receiver system which provides the fixed-path reference signal and also provides temperature compensation, a third "dummy" system employing an ultrasonic transmitter/receiver arrangement with apertured guide, to eliminate noise due to reflection from the corresponding guide in the principal ultrasonic system.

The present invention consists in apparatus for detecting defects in webs or sheets, including means defining a flow path for the web of for the sheets to be inspected, an ultrasonic transmitter arranged to direct ultrasonic energy towards the flow path in an inspection area, an ultrasonic receiver directed to receive ultrasonic energy from the inspection area, and signal analysing means responsive to the output of the receiver, in which the transmitter directs the ultrasonic energy towards the inspection area as a continuous wave and the signal analysing means provides an output signal in response to changes in the output of the receiver during the passage of the web or sheet indicative of a defect in the inspected web or sheet.

Because the signal analysing means is looking only for changes in the received ultrasonic energy, the apparatus can be considerably simpler than in a system comparing the phases of a sonic wave travelling a fixed reference distance and a sonic wave travelling a variable distance.

In a preferred form of apparatus embodying the invention, for an application in which it is particularly important to detect tears in banknotes, each banknote is passed over a first roller which contacts the central portion of the banknote and which has flared ends and then under a second roller of the same shape, the rollers causing opposite bending of the note in the direction at right-angles to the flow direction, as a consequence of which in the space between the rollers tears in the lateral edges of the banknote open up to allow the passage of ultrasonic energy from a transmitter on one side of the banknote to a receiver on the other side.

In another form, the detector is arranged to receive reflected ultrasonic energy. Again, if tear detection is of importance it is desirable to pass the banknote or other sheet over a roller in the inspection area. This results in a recognisable modification of the reflected ultrasonic energy, making the apparatus tear-sensitive, in addition to its sensitivity to surface deformations such as crinkle, fold lines and retained pins.

In order that the invention may be better understood, some examples of apparatus embodying the invention and an example of a circuit used in such apparatus will now be described with reference to the accompanying drawings, in which.

Figure 1:
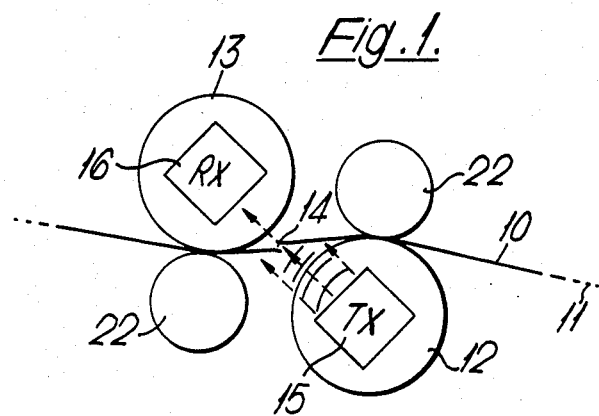
FIG. 1 illustrates diagrammatically a detection system utilizing the transmission of ultrasonic energy through tears.

In FIG. 1, a banknote 10 travelling along a flow path 11 passes over a first roller 12 and under a second roller 13 which are shaped, in a manner to be described, to cause the margins of the note to be deflected away from the plane of the centre of the note and thereby to open up tears 14 in the note, as indicated diagrammatically in FIG. 1. A transmitter 15 transmits ultrasonic energy towards the inspection area between the rollers and some of this energy passes through the tear and reaches the ultrasonic receiver 16.

Figure 2:
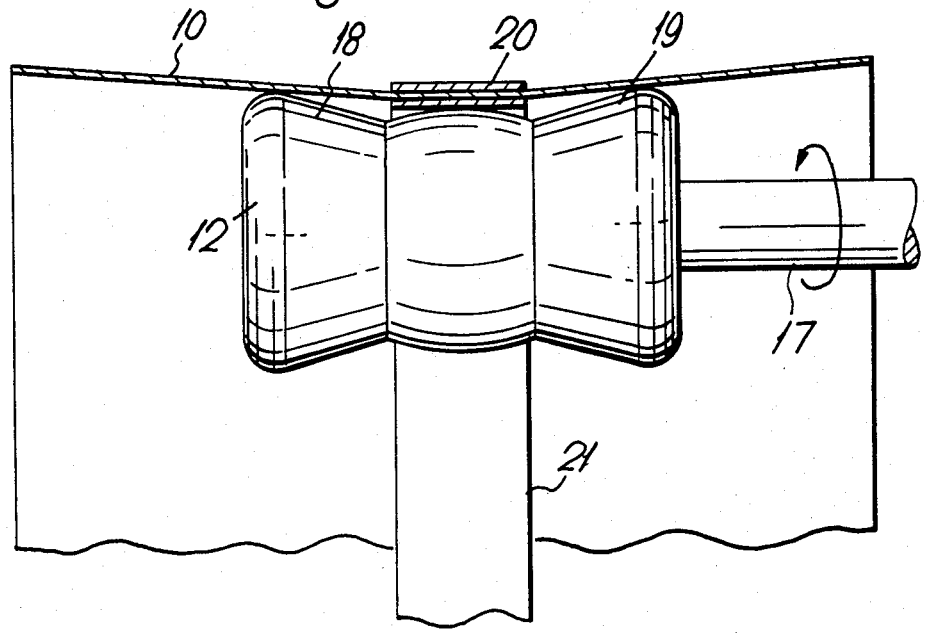
FIG. 2 shows the shape of rollers used in the arrangement of FIG. 1 to open the tears.

The form of the roller 12 is shown in FIG. 2: roller 13 has a similar shape. It will be seen that the roller 12, mounted on a shaft 17, has flared ends 18 and 19. Continuous belts 20, 21 engage the middle sections of the notes 10 and guide the notes through the apparatus. Smaller rubber rollers 22 (FIG. 1), which are not shaped in the manner shown in FIG. 2, may be used to keep the belts in contact with the rollers 12 and 13 if the sheets are of stiff paper; otherwise these rollers 22 are not essential. As the sheet passes over roller 12 and under roller 13, the flared ends of these rollers cause bending of the sheet (across its width) in different directions, and this causes any tears in the margins of the note to be opened, as shown at 14.

Figure 3:
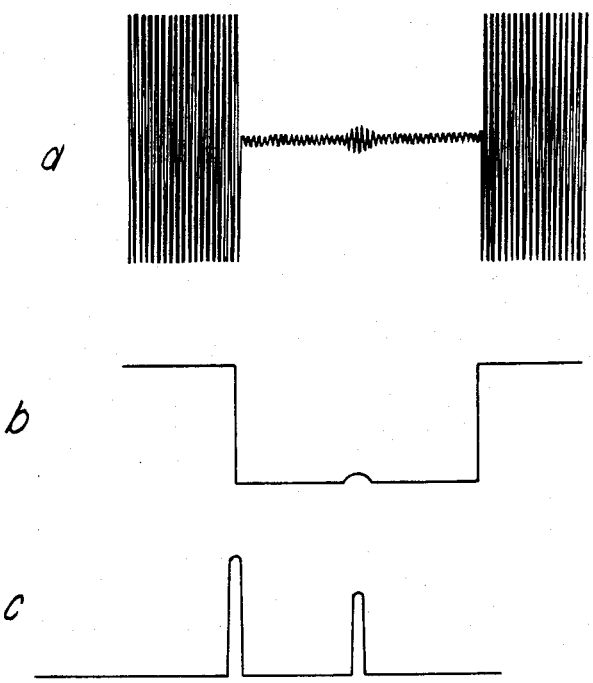
FIG. 3 shows waveforms derived from a receiver in the apparatus of FIG. 1.

Such opening allows a path for the ultrasonic energy, even though an optical path, in an optical detection system, would not necessarily be available. The path through the tear causes an irregularity of the received signal which can be detected by a spike filter. Typical waveforms derived from the receiver 16 are shown in FIG. 3. Waveform A illustrates the receiver output, before signal processing, and shows first a burst of ultrasonic energy before the arrival of the banknote; then a reduction to a very low level, when the banknote reaches the inspection area; next an increase in received ultrasonic energy from the low level, when the open tear reaches the inspection area; then a return to the low level when the tear has passed; and finally a return to the high level when the trailing edge of the banknote has passed through the inspection area. Waveform b is that obtained after demodulation of waveform a and waveform c shows the output of the spike detector.

This is responsive to a fall in the level of waveform b and shows one pulse corresponding to the arrival of the leading edge of the banknote and a second pulse corresponding to the departure of the tear from the inspection area.

Figure 4:
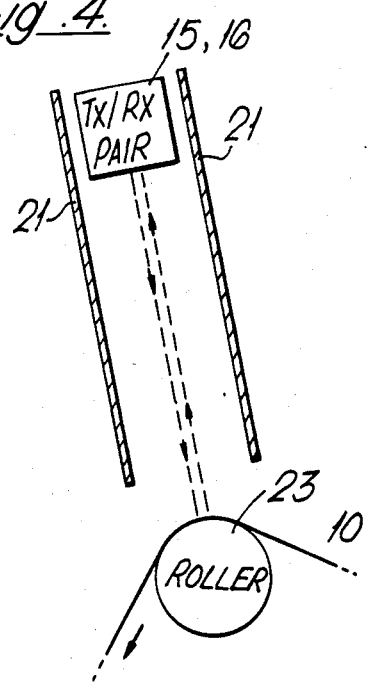
FIG. 4 shows a second arrangement of an ultrasonic transmitter/receiver system employing reflection of the ultrasonic energy by a sheet passing over a roller.

In an alternative arrangement, shown in FIG. 4, a reflective system is used. A continuous wave single frequency ultrasonic signal is projected at the note 10, which in this case passes over a roller 23 in the inspection area. In this arrangement, the transmitter/receiver pair are screened by a wall 25 to provide a coarse focus at the "illuminated" zone and to reduce spurious signals, such as signals from moving parts of the machine, from being received by the ultrasonic transducer 15, 16, in any significant magnitude. In FIG. 4, a de-alias bridge circuit is connected between the transducer, on the one hand, and the receiver pre-amplifier and transmitter oscillator, on the other hand.

Figure 5A:
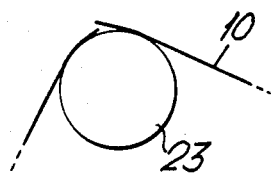
FIGS. 5A, 5B and 5C illustrate the different ways in which the roller can affect a tear in the sheet.
Figure 5B:
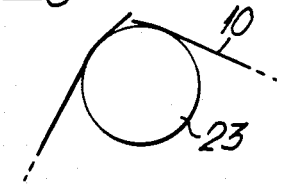
Figure 5C:
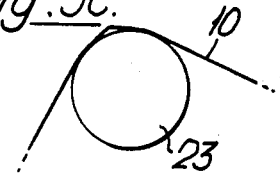

The use of a roller 23 at the inspection area also makes the apparatus of FIG. 4 particularly suitable for tear detection. The ways in which adjacent edges of the tear in the note may behave when passing over the roller are illustrated in FIGS. 5A, 5B and 5C. In FIGS. 5A and 5B, one side of the tear overlaps the other; in FIG. 5C neither side of the tear is overlapping but both sides leave the roller. With any of these forms of behaviour there is a characteristic modification of the reflected ultrasonic energy. For FIGS. 5A and 5B, interference will take place due to the difference in path length between the ultrasonic transducer and the two sides of the tear. For FIG. 5C, the tear will appear to be a surface deformation, as both sides of the tear leave the roller.

Defects in the form of folds, or the presence of pins in notes, also result in modification of the reflected signal as the note passes over the roller through the inspection area. Generally, the requirement is simply to detect the defect and it does not matter whether the defect is a fold or a tear. If discrimination is required, it may in some cases be useful to have two pairs of transducers, one on each side of the note and to compare their outputs.

Where the detection of tears is important, it may be advantageous in the reflective system also to pass the note over a roller with flaring ends. This reduces signal changes due to folds while allowing changes due to tears.

Figure 6:
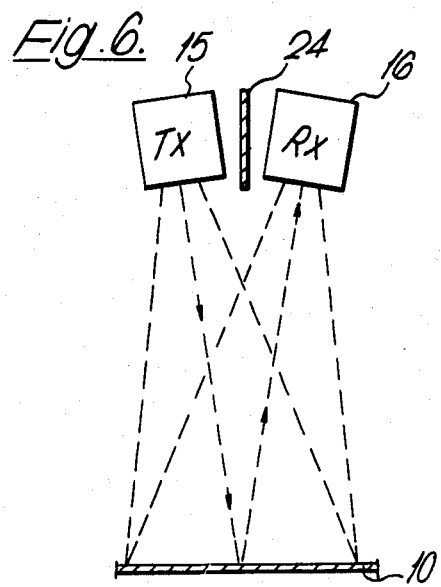
FIG. 6 shows a third transmitter-receiver system employing reflection of ultrasonic energy.

A third arrangement is shown in FIG. 6, in which the transmitter 15 and a receiver 16 are separated by a screen 24 to reduce their defect interaction and in which the note 10 passes along a flat flow path. As in FIG. 2, the notes are fed by a centre-belt transport and two pairs of transducers are provided for examining respective opposite edges of the note.

In analysing electrical signals derived from the received ultrasonic energy, several factors have to be taken into account. The wavelength of the ultrasonic signal (typically 8.5 mm at 40 kHz) is such that it is comparable to the size of imperfections in the note surface. Thus, assuming the transmitter to be a point source and that there is no transmissive or reflective scattering, if a note gave the maximum reflected signal in one position, then because of interference between the transmitted and reflected waves it would give a minimum reflected signal when a quarter wavelength closer to or further from the signal source. In practice, the transmitter is not a point source, has a finite beam width and causes both scatter and a wide "illumination" area. There are therefore many different paths possible for the reflected wave and this results in interference between different reflected waves.

Also, with a simple note transport it may not be possible to ensure that each note follows exactly the same path and so the reflected signal may not always be the same for any two passes of the same note. However, these difficulties are overcome in the present invention, in which the signal processing circuit detects changes of the received signal in amplitude and phase rather than specific levels. It will be appreciated that in a reflective system all phase changes produce an implicit amplitude change due to interference. It is generally simpler to use amplitude demodulation than phase demodulation.

Figure 7:
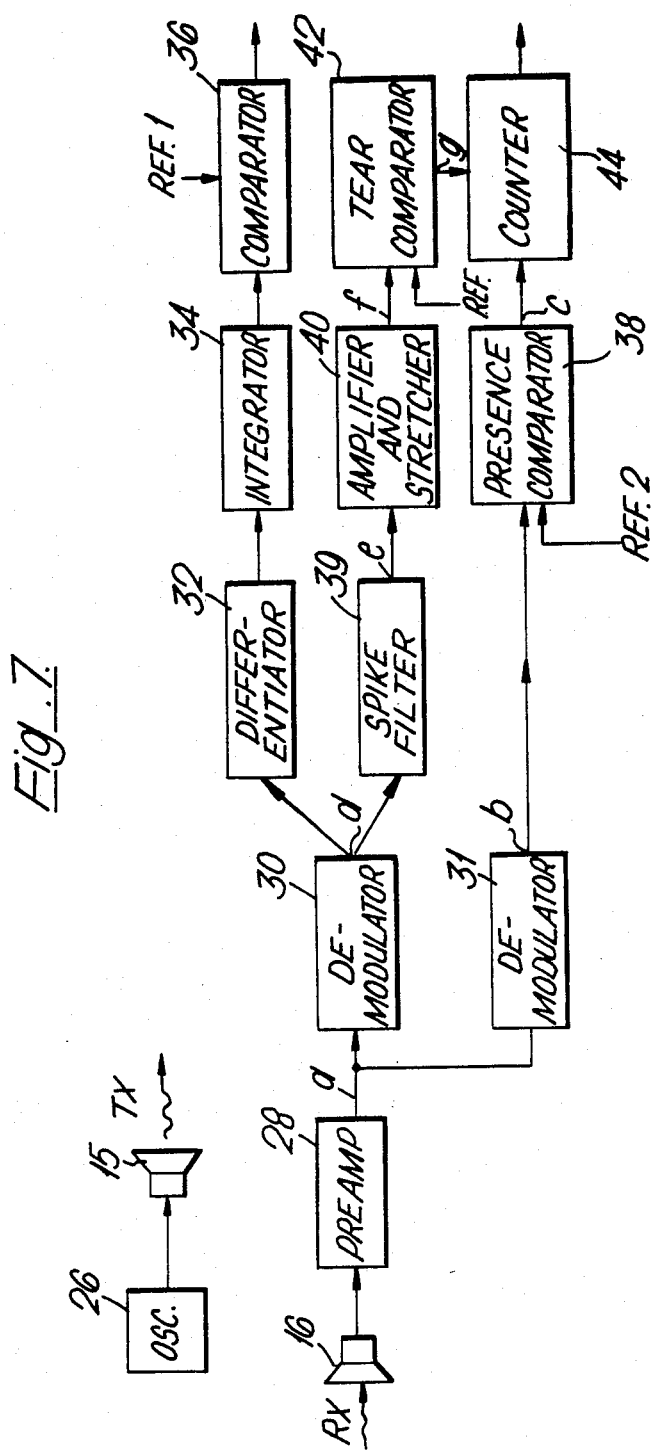
FIG. 7 is a block diagram of a signal-analysing circuit.

FIG. 7 is a block diagram of a circuit which may be used with the transducer pair of FIG. 4.

In the transmitter, an oscillator 26 feeds the transducer 15. The oscillator need not have a sinusoidal output but it may be desirable to incorporate the frequency trimming adjustment as it is easier to adjust the transmitter frequency than to adjust the receiver response. Additionally, the frequency trimming adjustment can be used when the apparatus is initially set up to achieve maximum received signals with a note of uniform smoothness stationary in the note transport system.

Figure 8:
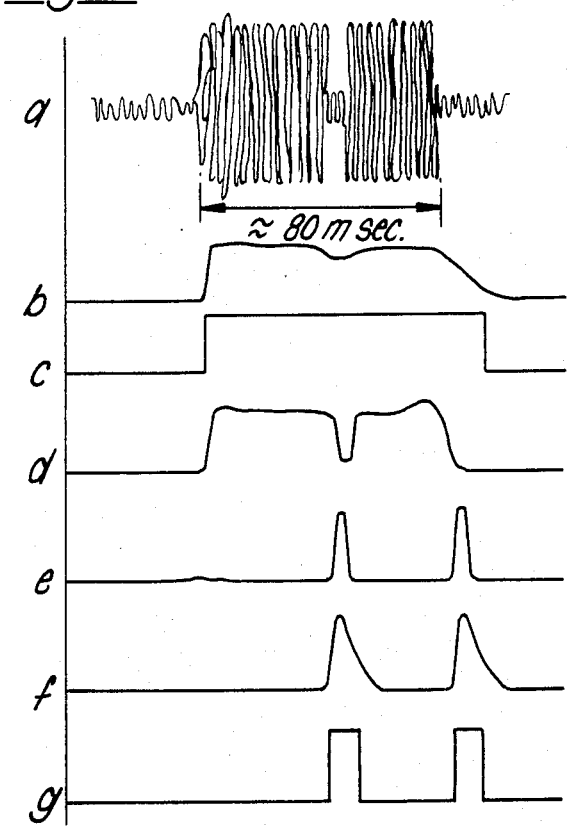
FIG. 8 is a diagram showing waveforms which exists at points in the circuit of FIG. 7.

At the receiver, the reflected ultrasonic energy is converted into an electric signal by means of transducer 16 and the signal passes through a pre-amplifier 28; this pre-amplifier may incorporate some form of loose tuning (for example a circuit using a band-pass filter) to reduce spurious responses. The output of the pre-amplifier is illustrated in waveform a of FIG. 8. This signal is applied to demodulator circuits 30 and 31, each including a capacitor/diode/resistor circuit. In this example, the received signals are used for the detection of both tears and "crinkle", i.e. multiple folds in a note. The waveforms at the outputs of demodulators 30 and 31 as shown in FIGS. d and b respectively. It will be seen that the demodulator 31 includes a larger capacitance and is consequently relatively insensitive to the tear indicated by the reduction in signal level part-way through the passage of the note in waveform a. The output of the demodulator 31 indicates "note presence" and is applied to a presence comparator 38, in which it is compared with a given threshold signal REF. 2, to obtain waveform c of FIG. 8.

To detect crinkle, the output of the demodulator 30 passes through a differentiator 32 to reach an integrator 34, the output of which indicates the overall energy of the crinkle signal. This signal resulting from the integration process goes to a comparator 36, in which it is compared with a programmed reference or threshold signal REF1. When the integrated signal reaches the threshold level, a logic signal indicative of excessive crinkle is sent to a controlling processor, which provides the appropriate indication or acts to deflect the note into a flow path different from that provided for notes in good condition.

For the detection of tears, both of the demodulators 30 and 31 are used. The output of the demodulator 30 is applied to a spike filter 39 which provides at its output the waveform e of FIG. 8. The spike filter is a 5 millisecond filter sensitive only to a fall in the contour signal. Thus in waveform e, there is a spike corresponding to the fall in the demodulator waveform when the tear is reached and a spike corresponding to the trailing edge of the note. This signal is applied to an amplifier and stretcher circuit 40, the output of which is shown in waveform f of FIG. 8, and the amplified and stretched signal is applied to the tear comparator 42. In comparator 42 the waveform f is compared with a predetermined reference voltage REF, to provide at the output of the comparator the signal shown in waveform g of FIG. 8. Thus, the latter waveform provides, for a note free from tears, a single pulse corresponding to the trailing edge of the note. If there is more than one pulse it is indicative of a tear in the note. Waveform g and waveform c are applied to a counter 44 in a microprocessor which determines when the additional pulse is present and provides a corresponding "defect" signal. The counter may be cleared by a waveform derived from the "note present" waveform c of FIG. 8. Alternatively, a clearing signal could be derived from a third ultrasonic transducer positioned on the far side of the note and receiving a direct transmitted ultrasonic wave in the absence of a note.

Folds and pins will in many case be sensed by the tear detector described above. If desired, such detection can be supplemented by a further detector aimed at a portion of the flow path where the note is not passing around a roller.

A further embodiment of the invention utilises Doppler shift of the reflected frequency, giving an output proportional to the velocity of relative movement of the sheet and inspection zone. The signal analysing circuit is then designed to use a method of demodulation (for example slope detection) which will give an output varying with change of note contours but which still enables the detector to be respond to interference changes.

It will be seen that the ultrasonic detection system permits the sensing of defects which are difficult to sense by other means. For example, surface deformations are difficult to sense optically and some deformations, for example crinkle are difficult to detect mechanically.

Although the circuit of FIG. 7 is designed to use with the apparatus of FIG. 4, the same circuit (with the exception of box 32, 34 and 36) can also be used with the apparatus of FIG. 1.

I claim:

1. In apparatus for detecting defects in webs or sheets, and having means defining a flow path for the web or for the sheets to be inspected, the combination of:
   an ultrasonic transmitter arranged to direct ultrasonic energy towards the flow path in an inspection area;
   an ultrasonic receiver directed to receive ultrasonic energy from the inspection area;
   and signal analysing means (FIG. 7) responsive to the output of the receiver;
   the transmitter directing the ultrasonic energy towards the inspection area as a continuous wave and the signal analysing means providing an output signal in response to changes in the output of the receiver during the passage of the web or sheet indicative of a defect in the inspected web or sheet; and wherein the receiver includes means defining in the inspection area a flow path which is convex in the longitudinal direction of the flow path, whereby the sheet or web is caused to assume a convex bend in the area in which the ultrasonic energy impinges upon it.

2. Apparatus in accordance with claim 1, in which the ultrasonic transmitter is arranged on one side of the flow path and the ultrasonic receiver is arranged on the other side of the flow path, and comprising in the vicinity of the inspection area a roller over which the sheet or web is passed, the roller having ends shaped to cause the marginal portion of a web or sheet to be deflected out of the plane of its central portion, the change in the cross-sectional form of the sheet or web causing marginal tears to open allowing ultrasonic energy from the transmitter to pass through the tears to the receiver.

3. Apparatus in accordance with claim 2, in which the roller has end portions which increase in diameter towards the ends.

4. Apparatus according to claim 2, comprising two rollers with similarly shaped ends, spaced along the flow path, the flow path passing over one roller and then under the next, whereby a tear in the sheet or web passing along the flow path opens in the space between the two shaped rollers.

5. Apparatus in accordance with claim 1, in which the receiver is arranged to receive ultrasonic energy reflected from the sheet or web in the inspection area.

6. Apparatus in accordance with claim 1, comprising a roller defining the flow path in the inspection area, the sheet or web passing over the roller.

7. Apparatus in accordance with claim 6, in which the roller is formed with flared ends, whereby the effect of folds in a sheet or web on the received signal is reduced but the effect of tears is not reduced.

8. Apparatus in accordance with claim 1, comprising a belt system extending along the central portion of the flow path for feeding the sheet or web along the flow path.

9. Apparatus in accordance with claim 1, comprising a circuit receiving electric signals from the ultrasonic receiver, means for detecting abrupt changes in the signal such as are caused by the edge of a sheet or a tear in the sheet, and means for counting the abrupt changes during the passage of a sheet to ascertain whether the number of such changes indicates at least one such change indicative of a defect between the leading and trailing edges of the sheet.

10. Apparatus in accordance with claim 1, for detecting crinkle in a sheet, in which the signal analyzing means further comprises a demodulator receiving an electric signal derived from the ultrasonic receiver, a differentiator for deriving signals related to the positions of the crinkled portions of the note, an integrator connected to receive the signals from the differentiator, and a comparator comparing the integrator output with a preset or programmed crinkle level.

* * * * *